United States Patent [19]

Ahn et al.

[11] Patent Number: 5,983,702
[45] Date of Patent: Nov. 16, 1999

[54] COMPOUND TESTING MACHINE FOR TESTING VARIOUS MECHANICAL PROPERTIES USED FOR OPTICAL CONNECTOR

[75] Inventors: Seung Ho Ahn; Sang Ho Park; Oh Gone Chun; Myung Yung Jeong; Tae Goo Choy, all of Daejeon; Han Dae Cho, Kyunggi-do, all of Rep. of Korea

[73] Assignees: Electronics and Telecommunications Research Institute, Daejeon; Korea Telecom, Seoul, both of Rep. of Korea

[21] Appl. No.: 08/979,607

[22] Filed: Nov. 26, 1997

[30] Foreign Application Priority Data

Dec. 20, 1996 [KR] Rep. of Korea ............ 96-69260

[51] Int. Cl.[6] ........................................... G01N 3/30
[52] U.S. Cl. .......................... 73/12.06; 73/826; 73/800
[58] Field of Search .......................... 73/800, 812, 826, 73/12.01, 12.06, 12.13; 324/538

[56] References Cited

U.S. PATENT DOCUMENTS

| | | | |
|---|---|---|---|
| 4,468,117 | 8/1984 | Hartouni et al. | 356/73 |
| 5,097,213 | 3/1992 | Hunting et al. | 324/538 |
| 5,266,059 | 11/1993 | Taylor | 324/754 |
| 5,390,534 | 2/1995 | Feeney | 73/79 |
| 5,424,634 | 6/1995 | Goldfarb et al. | 324/158.1 |
| 5,431,060 | 7/1995 | Lauren | 73/831 |

*Primary Examiner*—Max Noori
*Attorney, Agent, or Firm*—Cohen, Pontani, Lieberman & Pavane

[57] ABSTRACT

A compound testing machine for testing mechanical properties used for an optical connector does not additionally have each testing machine for each of mechanical properties (such as a tensile force including both a straight pull and a side pull, a flex, a twist and an impact) in testing a mechanical property between optical connectors and other mechanical property between optical fibers of the optical connectors, and includes only one testing machine for simultaneously testing various mechanical properties in order to enhance a test machine's efficiency. The compound testing machine includes: a rotation part which includes a test specimen fixing portion for fixing a test specimen, a cable connected to the test specimen, and a load applying portion connected to the cable so as to provide a predetermined load to the test specimen, receives a driving force of an electric motor, and measures a tensile force and a flex; and an impact testing part which is mounted to one side of the rotation part, drops the test specimen while freely adjusting a height of the test specimen, and thus performs an impact test.

13 Claims, 5 Drawing Sheets

COMPOUND TESTING MACHINE FOR TESTING VARIOUS MECHANICAL PROPERTIES USED FOR OPTICAL CONNECTOR

BACKGROUND OF THE INVENTION

1. Field of the Invention

The present invention generally relates to a compound testing machine for testing mechanical properties of an optical connector used for connecting or switching the optical lines in an optical communication system. More particularly, it relates to a compound testing machine for testing mechanical properties used for an optical connector, which compositely evaluates mechanical properties with respect to a tensile force including both a straight pull and a side pull, a flex, a twist and an impact among various mechanical properties of the optical connector, by using one machine.

2. Description of the Conventional Art

In recent times, many kinds of the optical connectors used for achieving a connection between the optical lines have been developed. These optical connectors mostly have a plug-adapter-plug structure, and mainly use a push-pull structure as a connection method.

Excepting a single-fiber optical connector, due to a packaging density and a working efficiency, a multi-fiber optical connector has been used for a connection of a super multi-fiber cable used in an optical subscriber's network service.

Many kinds of the multi-fiber optical connectors have been manufactured on a commercial scale, together with developing all optical fiber ribbon.

That is, the multi-fiber optical connectors including four-fiber, eight-fiber, twelve-fiber and sixteen-fiber have been developed in response to the optical fiber ribbon's shape. Recently, a new multi-fiber optical connector including eighty-fiber for the super multi-fiber optical cable has been developing.

The new optical connector can be used for achieving a connection between the multi-fiber optical cables and for subscribers as well, and can also be used for a system such as a distributor. In addition, the optical connector can be used for an optical LAN (local area network), a parallel connection between computers, a data-link, or a connection of optical components such as an LD array. Various optical fibers (e.g., optical cables) having a single-fiber and a multi-fiber are used for the above purposes.

Therefore, a testing machine to estimate mechanical properties such as a tensile force of the optical connector connected to the above various optical fibers should be designed.

The testing machine for testing the mechanical properties of the optical connector generally teaches a test method to the users, and is designed to estimate the mechanical properties. A test standard for the testing machine only defines a test condition, a brief construction and a function of the testing machine.

Accordingly, to satisfy the test standard, the apparatus needed to test each of mechanical properties has been respectively manufactured in various shapes.

In case of foreign countries, the apparatus for testing each of the mechanical properties has been separately manufactured in response to each mechanical property.

The EIA (Electronics Industries Association)—455 standards for internationally defining a test condition and a test method of optical components does not include a content about a detailed structure of the apparatus, and only includes a content about the test condition. Also, the EIA—455 standard provides that some test items can be examined by a user's handling, but the user should pay close attention to this handling test.

SUMMARY OF THE INVENTION

Accordingly, the present invention is directed to a compound testing machine for testing mechanical properties used for an optical connector that substantially obviates one or more of the problems due to limitations and disadvantages of the conventional art.

It is an object of the present invention to provide a compound testing machine for testing mechanical properties used for an optical connector, which does not have a plurality of testing machines for each of mechanical properties (such as a tensile force including both a straight pull and a side pull, a flex, a twist and an impact) in testing a mechanical property between optical connectors of various shapes and other mechanical property between optical fibers of the optical connectors, and includes only one testing machine for simultaneously testing various mechanical properties, thereby enhancing a test machine's efficiency.

It is another object of the present invention to provide a compound testing machine for testing mechanical properties used for an optical connector, which accurately measures and estimates mechanical properties of the optical connector by using a compound testing machine precisely fabricated, maintains a reliability of the measured mechanical properties, and thus obtains various mechanical properties.

To achieve the above objects, in an apparatus for measuring and estimating mechanical properties of an optical connector used for an optical communication system, a compound testing machine for testing mechanical properties used for an optical connector includes:

- a rotation part which includes a test specimen fixing portion for fixing a test specimen, a cable connected to the test specimen, and a load applying portion connected to the cable so as to provide a predetermined load to the test specimen, receives a driving force of an electric motor, and measures a tensile force and a flexion; and
- an impact testing part which is mounted to one side of the rotation part, and drops the test specimen while freely adjusting a height of the test specimen, thereby performing an impact test.

Additional advantages, objects and other features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

The preferred embodiment of the present invention will become apparent from a study of the following detailed description, when viewed in light of the accompanying drawings.

Figure 1:
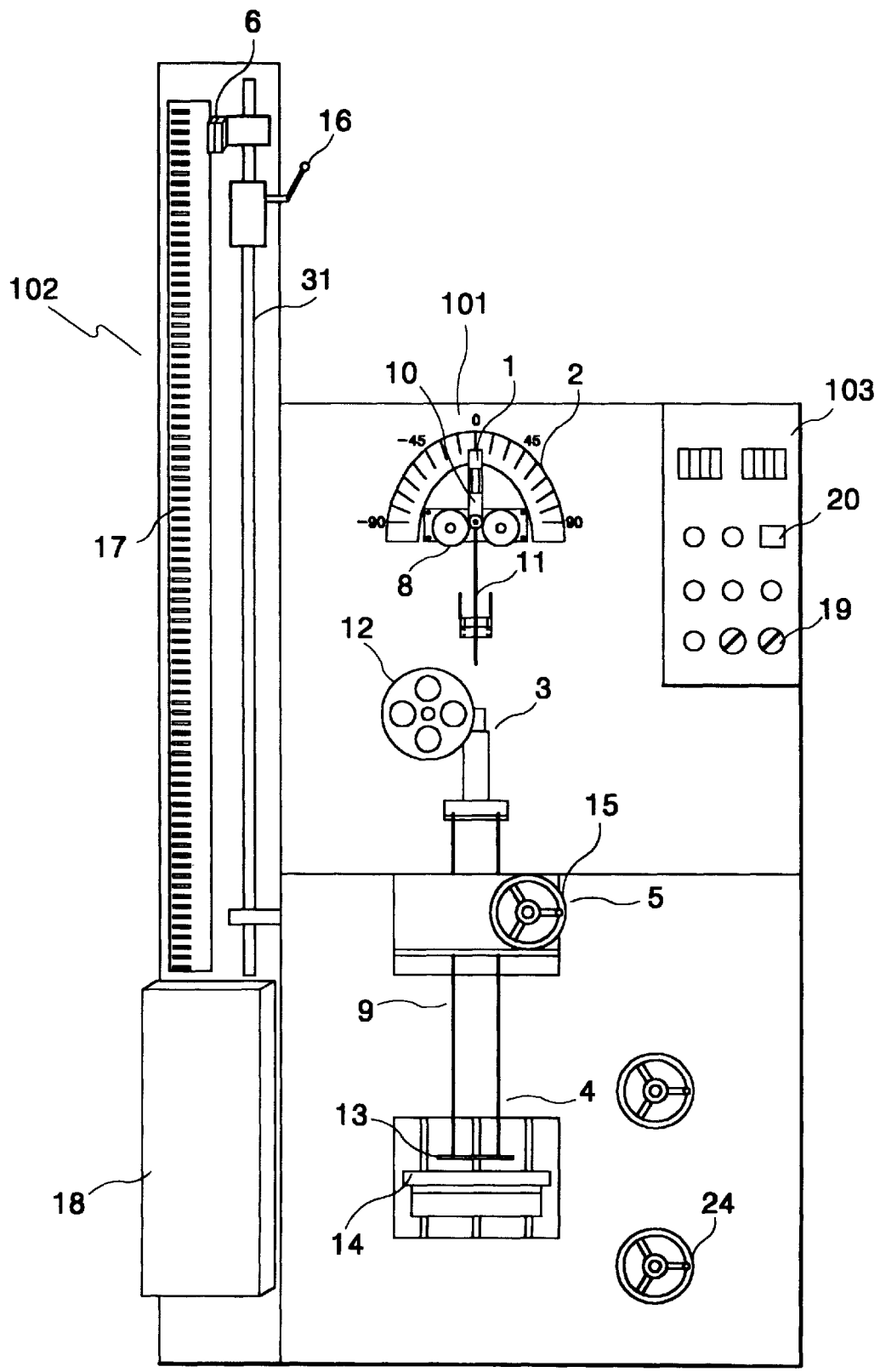
FIG. 1 shows a compound testing machine for testing mechanical properties used for an optical connector in accordance with the present invention.

FIG. 1 shows a compound testing machine for testing mechanical properties used for an optical connector in accordance with the present invention.

As shown in FIG. 1, reference numbers 1 and 6 indicate test specimen fixing portions, a reference number 2 indicates an angle meter, a reference number 3 indicates a capstan, a reference number 4 indicates a load applying apparatus, a reference number 5 indicates a twist apparatus, a reference number 8 indicates a cable guide, reference numbers 9 and 31 indicate metal rods, a reference number 10 indicates a test specimen, a reference number 11 indicates a cable, a reference number 13 indicates a load support plate, a reference number 14 indicates a support plate, a reference number 15 indicates a rotary knob, a reference number 19 indicates a power switch, a reference number 20 indicates an alarm device, a reference number 101 indicates a rotation part, a reference number 102 indicates an impact testing part, and a reference number 103 indicates a control unit.

By using only one machine, a compound testing machine for testing mechanical properties used for an optical connector performs a straight pull tensile force test and a side pull tensile force test, a flex test for horizontally bending a connection portion between the optical connector and the cable, a twist test for twisting the cable connected to the optical connector, and an impact test.

Referring to FIG. 1, the compound testing machine includes:

a rotation part 101 which is driven by an electric motor (not shown) in order to perform a tensile force test, a flex test and a twist test;

a control unit 103 which is mounted to one side of the rotation part 101, and controls a number of tests and a test speed; and an impact testing part which is mounted to other side of the rotation part 101, and performs an impact test by dropping a test specimen simultaneously with controlling a height of the test specimen.

More specifically, the rotation part 101 includes:

a test specimen fixing portion 1 which fixes a test specimen 10 in order to perform both a tensile force test of a straight pull and a side pull and a flex test according to a fixed angle of the test specimen;

an angle meter 2 which reads test angles of a flex and a side pull tensile force;

a capstan portion 3 which fixes a cable 11 in order to transmit a load to the test specimen 10;

a load applying apparatus 4 which provides a proper load to the test specimen 10; and a twist apparatus 5 which turns the load applying apparatus 4 by a handling operation, and thus provides a twist force to the test specimen 10.

The angle meter 2 has a cable guide 8 for preventing a rocking of the cable 11 connected to the test specimen 10. A capstan portion 3 is connected to the load applying apparatus 4 through two metal rods 9. A capstan 12 winds and fixes the cable 11 thereon within the range in which there is no influence by a bending in the cable 11 connected to the test specimen 10.

The load applying apparatus 4 includes:

a load support plate 13 connected to the lower part of the metal rods 9; and a support plate 14 for supporting the load support plate 13 not to apply a load to the test specimen 10 before the test.

The twist apparatus 5 includes a rotary knob 15 for horizontally twisting two metal rods 9 connected to the load applying apparatus 4 for the twist test.

The control unit 103 includes a power switch 19 of the testing machine and an alarm device 20. Since a bending angle of the test specimen is determined in the control unit 103, the control unit 103 generally controls test condition of a tensile force, a flex and a twist which are measured by the rotation part.

Figure 2:
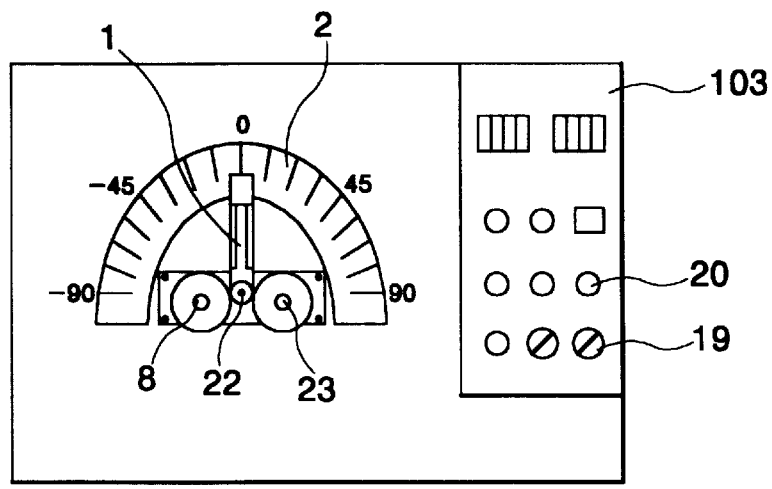
FIG. 2 shows a testing machine for testing a tensile force and flex in accordance with the present invention.

For an impact test, the impact testing part 102 includes a lever 16 for adjusting a height, and a test specimen fixing apparatus 6 and a height checking graduations 17. Also, the impact testing portion 102 includes a steel plate 18 on which an impact generated by the test specimen's drop is applied. FIG. 2 shows a rotation part 101 and the control unit 103. As shown in FIG. 2, angles ranging from 0° to ±100° are indicated on the angle meter 2 necessary for a flex test and a side pull tensile force. Here, the angle 0° is used to determine a zero point before the test. The control unit 103 performs a test by using a desired angle (e.g., right-and-left 90°) according to an internal program. A horizontal flex of the test specimen 10 achieves an accurate symmetric motion as much as a desired angle by an electric motor.

In the test specimen fixing portion 1 for performing a flexion test and a tensile force test and the angle meter 2 for checking a test angle, the test specimen fixing portion 1 precisely adjusts an angle ranging from 0° to 100° by using the electric motor. The test specimen fixing portion 1 is located at a position of 0° in a direction of a vertical line, thereby making both a straight pull tensile force test and a twist test possible. For a flex test, the test specimen fixing portion 1 is maximally rotated by a right-and-left 100°, and thus satisfies the range of ±90° required by the standard. A rotation shaft 22 is included in the lower part of the test specimen fixing portion 1. A circular guide 8 for preventing the cable 11 from rocking during the test is included in the right and left sides of a rotation shaft 22. A position of the guide 8 can be adjusted by a screw 23. The screw 23 may be removed, if necessary.

Figure 3:
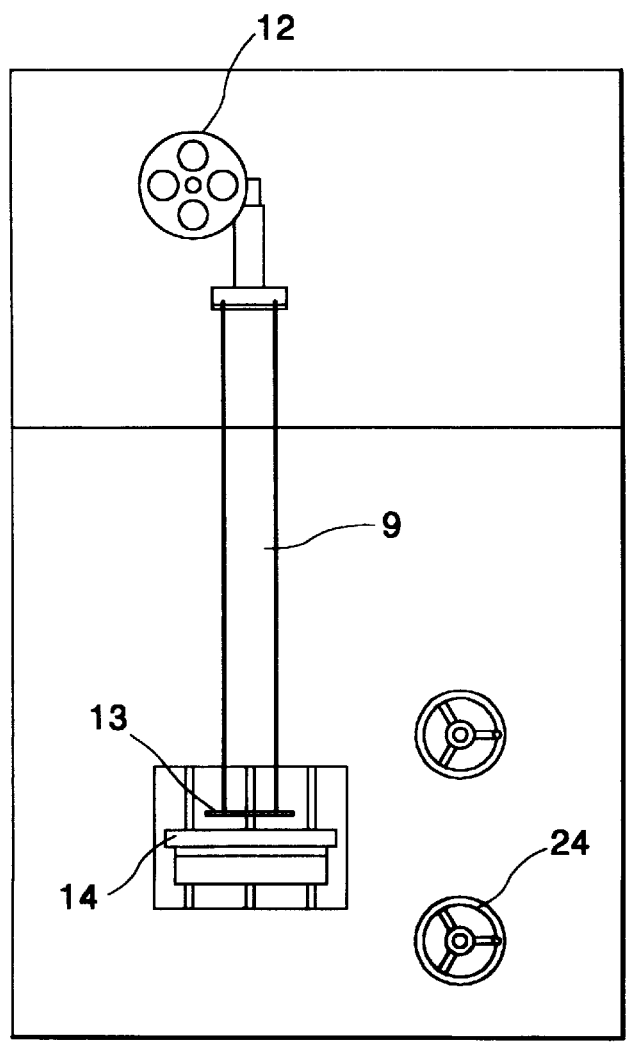
FIG. 3 shows a load applying apparatus in accordance with the present invention.

FIG. 3 shows a load applying apparatus 4 in accordance with the present invention.

Referring to FIG. 3, the load applying apparatus 4 includes:

a load support plate 13 which is connected to a capstan 12 of the capstan portion 3 for fixing a cable of the test specimen 10, and puts a load thereon so as to make a load be applied thereon;

two metal rods 9 for connecting the capstan 12 to the load support plate 13; and a support plate 14 which supports the load support plate 13 in order to not make the load be applied to the test specimen 10 before the test, drops the load support plate 13 by using a rotary knob 24 in order to perform the test, and thus causes the load to be applied to the support plate 14. The capstan 12 is made of a light material using nylon, so that a total weight is not beyond a minimum applying load. The load applying load 4 is made of a light material as of an aluminum 6061.

Figure 4:
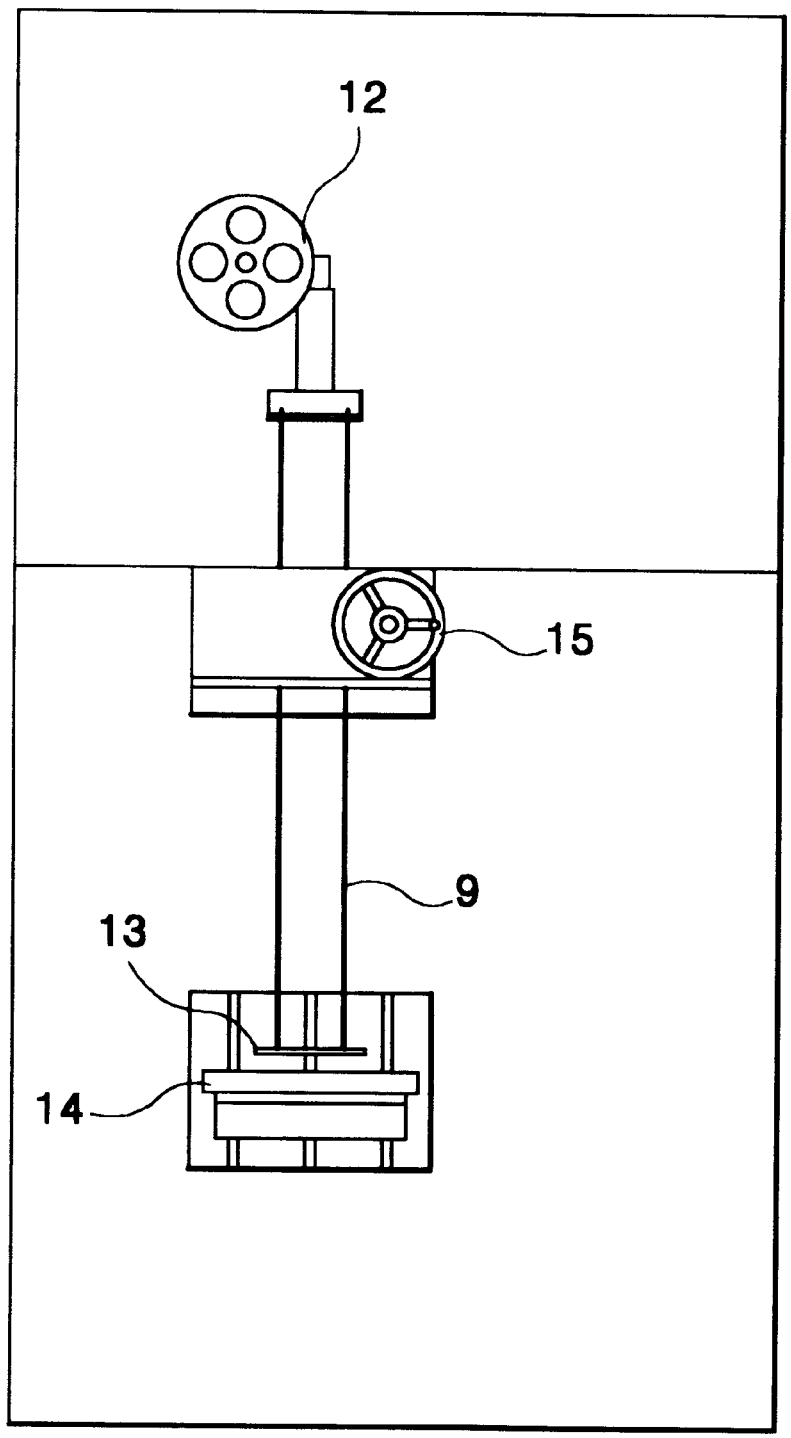
FIG. 4 shows a twist apparatus in accordance with the present invention.

FIG. 4 shows a twist apparatus 5 in accordance with the present invention.

As shown in FIG. 4, when the twist apparatus 5 rotates a rotary knob 15 through a rotary gear (not shown), two metal rods 9 connected between the plumb support plate 13 of the load applying apparatus 4 and the capstan 12 are twisted by a desired angle.

If the rotary knob 15 is turned by using a helical gear, the twist force ranging from −180° to +180° is generated. Since two metal rods 9 are connected to both the capstan 12 and the load applying apparatus 4 through two symmetrical guide holes formed on a rotary plate, the rotary knob 15 is turned. Accordingly, the capstan 12 and the load applying apparatus 4 are rotated, a turning effect is transmitted to a cable 11 connected to the test specimen 10, two metal rods 9 are used to prevent a rocking during a rotation of the cable 11.

Figure 5:
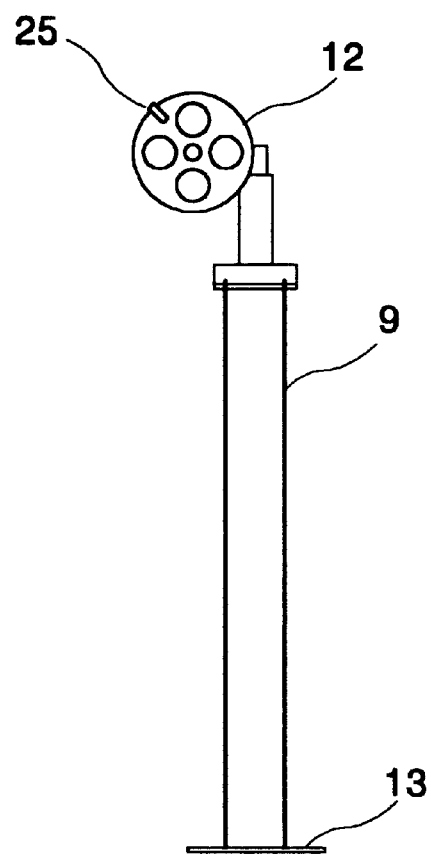
FIG. 5 shows a capstan portion for fixing a cable so as to make a load be applied to a cable of a test specimen in accordance with the present invention.

FIG. 5 shows a capstan portion 3 for fixing a cable 11 in order to make a load be applied to a cable 11 of a test specimen 10.

The capstan portion 3 winds the cable 11 connected to the test specimen 10 on the capstan 12. The capstan 12 is connected to the load support plate 13. In order to make a light capstan, the capstan 12 is made of a nylon material, so that the capstan 12 has a weight below 50 grams. The capstan 12 maintains a proper diameter in order to prevent an influence of a bending when winding the cable 11. A urethane rubber is used in the inside of the capstan 12 in order to prevent the cable 11 from sliding. A groove 25 for treating a remaining cable 11 formed in the capstan 12. The groove 25 pulls out the cable 11 from the capstan 12, and fixes it.

Figure 6:
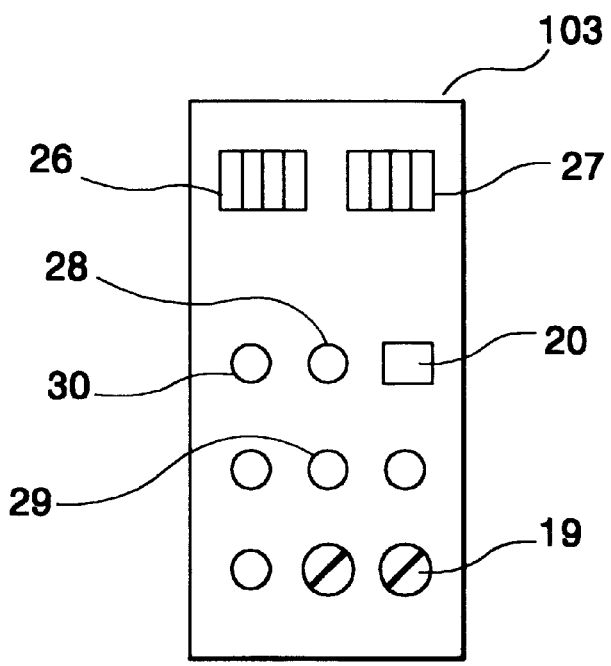
FIG. 6 shows a control unit in accordance with the present invention.

FIG. 6 shows a control unit 103 in accordance with the present invention. As shown in FIG. 6, the control unit 103 includes:

a power switch 19 of the testing machine;
an alarm device 20 for notifying a termination of the test;
a display portion 26 for displaying a right-and-left moving angle;
a digital instrumental panel 27 for displaying a number of revolution;
a switch for performing a test starting 28 or a test termination 29; and
a switch 30 for resetting a program.

Figure 7:
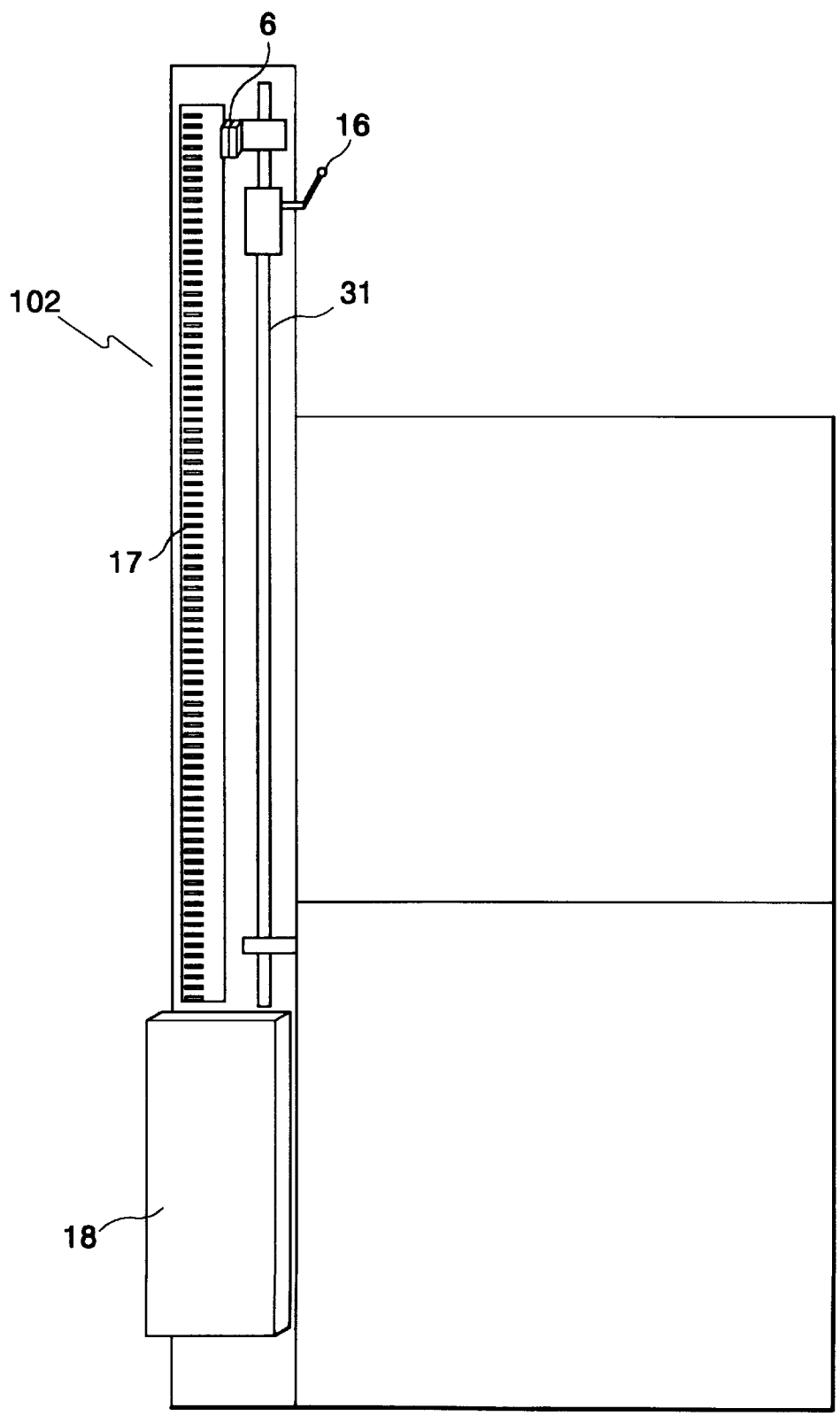
FIG. 7 shows an impact testing apparatus in accordance with the present invention.

FIG. 7 shows an impact testing apparatus 102 in accordance with the present invention.

As shown in FIG. 7, the impact testing apparatus 102 includes:

a fixing apparatus 6 for fixing the test specimen; and
a lever 16 for vertically controlling a height at which the impact is applied, and fixing the test specimen.

The lever 16 is guided by a metal rod 31, and is thus vertically moved. A steel plate 18 is positioned in the lower part of the impact testing apparatus 102. When both a graduation 17 for checking the height and the test specimen 10 are dropped, the test specimen 10 is collided with the steel plate 18, thereby generating an impact force on the steel plate 18.

As described above, the present invention relates to en apparatus for estimating mechanical properties of an optical connector used for connecting or switching transmission lines in an optical communication system. In the present invention, one testing machine simultaneously estimates a tensile force property, a flex property, a twist property, and an impact property, thereby simplifying a measuring time and a measuring procedure. Accordingly, the present invention obtains an efficiency in testing mechanical properties and an economical efficiency, and also performs a reliable accurate estimation about the mechanical properties by using the testing machine precisely manufactured.

Although the preferred embodiments of the present invention have been disclosed for illustrative purposes, those skilled in the art will appreciate that various modifications, additions and substitutions are possible, without departing from the scope and spirit of the invention as recited in the accompanying claims.

What is claimed is:

1. A testing machine for testing mechanical properties of an optical connector, comprising:

a rotation part including a test specimen fixing portion for fixing a test specimen, a cable connected to said test specimen, and load applying means connected to said cable for providing a predetermined load to said test specimen, receiving a driving force from an electric motor, and measuring tensile force and flex; and an impact testing part mounted to one side of said rotation part for freely adjusting an impact height of said test specimen and simultaneously dropping said test specimens.

2. The testing machine of claim 1, wherein said rotation part further comprises:

a capstan for applying a load to said test specimen, and winding said cable thereon within a range wherein said cable is not affected by bending; and metal rods connecting said capstan to said load applying means.

3. The testing machine of claim 1, further comprising:

twist force generating means including:

a rotary knob mounted between said capstan and said load applying mean for providing a horizontal twist force to a test specimen on which said load is applied; and a rotary gear for transmitting a turning force of said rotary knob to said metal rods and generating a desired twist force.

4. The testing machine of claim 1, wherein said test specimen fixing portion comprises:

a rotation shaft maximally rotated by about 100° in a horizontal direction by said electric motor; and an angle meter for measuring a rotation angle of said rotation shaft.

5. The testing machine of claim 1, further comprising:

a control unit mounted to one side of said rotation part for controlling said rotation part and said impact testing part.

6. The testing machine of claim 5, wherein:

said control unit controls a rotation angle of said test specimen for a tensile force test, thereby testing both a straight pull tensile force about said test specimen at an angle of about 0° and a side pull tensile force about said test specimen at an angle of about 90°, and determines a rotation angle and a number of revolutions for a flex test.

7. The testing machine of claim 3, further comprising:

guides mounted on both sides of a lower part of said angle meter, and formed as a mandrel for preventing rocking of said cable when said test specimen is horizontally moved.

8. The testing machine of claim 7, wherein each of said guides further includes:

a screw for horizontally adjusting an interval between said guides.

9. The testing machine of claim 1, wherein the load applying means comprises:

a load support plate connected to a lower part of said metal rods;

a support plate for supporting said load support plate so as not to apply a load to a test specimen before a test; and a rotary knob for vertically adjusting said support plate.

10. The testing machine of claim 2, wherein:

the capstan is made of a nylon material, has a predetermined diameter, and includes a urethane rubber mounted in an inner circumference thereof in order to prevent said cable from sliding thereon.

11. The testing machine of claim 2, wherein said capstan further comprises:

a groove of a predetermined size formed in said circumference and configured to pull out said cable from said capstan and to fix said cable; and a connection portion for connecting the capstan to the load applying means.

12. The testing machine of claim 3, wherein:

said twist force generating means includes a helical gear by which said rotary knob and said rotary gear are in a ratio of one to one, and is twisted from −180° to +180° according to said turning force of said rotary knob.

13. The testing machine of claim 1, wherein said impact testing part comprises:

a fixing portion for fixing said test specimen;

a lever for vertically adjusting the impact height of said test specimen and fixing said impact height;

a guide bar for guiding a vertical motion of said lever;

a graduation mounted to one side of said lever for measuring said impact height; and a steel plate mounted to a lower part of said guide bar for receiving an impact generated by a drop of said test specimen.

\* \* \* \* \*